United States Patent [19]
Sherman

[11] 4,344,428
[45] Aug. 17, 1982

[54] ORAL ENDOTRACHEAL TUBE PROTECTOR, AND METHODS OF CONSTRUCTING AND UTILIZING SAME

[76] Inventor: Stanley Sherman, 2543 Wickfield Rd., West Bloomfield, Mich. 48033

[21] Appl. No.: 122,872

[22] Filed: Feb. 20, 1980

[51] Int. Cl.³ ............................................. A61M 25/00
[52] U.S. Cl. ................... 128/207.14; 128/12; 128/DIG. 26
[58] Field of Search ............... 128/207.14, 207.15, 128/207.16, 207.17, 200.26, DIG. 26, 15, 4, 136, 348, 349 B, 350 R, 12

[56] References Cited

U.S. PATENT DOCUMENTS

| | | | |
|---|---|---|---|
| 3,599,642 | 8/1971 | Tindel | 128/207.14 |
| 3,616,799 | 11/1971 | Sparks | 128/207.15 |
| 3,713,448 | 1/1973 | Arro | 128/207.17 |
| 3,927,676 | 12/1975 | Schultz | 128/207.17 |
| 4,166,467 | 9/1979 | Abramson | 128/207.14 |
| 4,167,946 | 9/1979 | Sandstrom | 128/207.17 |
| 4,223,671 | 9/1980 | Muto | 128/DIG. 26 |
| 4,270,529 | 6/1981 | Muto | 128/200.26 |

FOREIGN PATENT DOCUMENTS 1399093  6/1975  United Kingdom ........... 128/207.15

OTHER PUBLICATIONS

Giuffrida et al., "Bizzari-Giuffrida Endoesophageal Tube", 1959, *Davol Catalogue*.

*Primary Examiner*—Henry J. Recla
*Attorney, Agent, or Firm*—Irving M. Weiner; Pamela S. Burt; John L. Shortley

[57] ABSTRACT

An improved oral endotracheal tube protector device for protecting and securing in place an endotracheal tube. The device includes a substantially straight, cylindrical tube member having a bore extending therethrough, with a circumferential band to indicate proper positioning of the device in close proximity to the proximal end, and circumferential ridges at the distal end to which tape is attached. In use, the tube protector is slidably placed over the endotracheal tube and advanced until the circumferential band engages the patient's teeth. The tube protector is then taped to the endotracheal tube, and to the patient's face.

10 Claims, 2 Drawing Figures

ORAL ENDOTRACHEAL TUBE PROTECTOR, AND METHODS OF CONSTRUCTING AND UTILIZING SAME

BACKGROUND OF THE INVENTION

1. Field of the Invention

The present invention relates generally to a device for use in connection with protecting and securing in place an endotracheal tube.

More particularly, the oral endotracheal tube protector in accordance with the present invention forms a part of an assembly which provides an air passageway free of obstruction. After the patient is intubated with a flexible endotracheal tube, the tube protector is placed over the endotracheal tube to prevent blockage of, or damage to, the endotracheal tube.

2. Description of Relevant Art

Prior art and conventional endotracheal tube protector devices have not been successful in providing a device which protects and secures in place an endotracheal tube while at the same time minimizes trauma to the patient and cost of manufacture. In particular, there has not been developed any generally acceptable endotracheal tube protector device which provides the aforementioned desirable advantages.

Illustrative of prior art devices in the field of endotracheal tube devices are those disclosed in U.S. Pat. Nos. 3,606,669; 4,068,658; 4,112,936 and 4,148,308.

Also illustrative of prior art devices are: the Olympic ENDO-LOK manufactured by the Olympic Medical Corporation of Seattle, Washington; the BITE BLOCK AND DENTAL GUARD manufactured by the American Hospital Supply Corporation of McGraw, Illinois; and the ENDOTRACHEAL TUBE HOLDER and AIRWAYS manufactured by Portex Incorporated, of Wilmington, Maine.

Kemble U.S. Pat. No. 3,606,669 discloses an endotracheal tube device consisting of an outer tube made of rigid plastic that is bent to the desired radius, and a flexible inner tube. The device is presumably intended to be of sufficient length and curvature to allow insertion of the device into the throat of the patient. It is held in place by an elastic band attached to a plate at the distal end of the outer tube.

Berman U.S. Pat. No. 4,068,658 discloses an endotracheal tube device consisting of a tube made of plastic of sufficient rigidity to allow it to retain a curved shape, yet flexible enough to allow it to bend along a longitudinal hinge. The tube has sufficient length and curvature to allow insertion into the patient's throat. A longitudinal opening allows the device to be removed while the tube is left in place. A flange at the distal end of the longitudinal opening plug functions as a bite block to prevent outward displacement of the device.

Blachly U.S. Pat. No. 4,112,936 discloses an airway assembly for use in electro-convulsive therapy of mental patients and the administration of gaseous anesthetic to edentulous patients. A U-shaped block of resilient material having upper and lower teeth-engaging surfaces is provided through which an oval aperture is formed at the front between such teeth-engaging surfaces. The aperture receives a tongue depressor-type airway tube that extends through the aperture.

Sayer U.S. Pat. No. 4,148,308 discloses a combination mouthpiece and tongue retractor for use by a conscious person who can voluntarily close his lips around the device. Sayer provides a tubular member which is either circular or rectangular in shape. A port extends from the bottom of the tubular member at a 45° angle, creating a secondary air passageway. A blade-like member extends from the bottom of the device at the proximal end to form a tongue retractor. Gun-barrel rifling or vanes are provided in the interior walls to facilitate medication administration. The diameter of the tubular member is large because the device is primarily used in the evaluation of respiratory processes, and a narrow diameter tube would adversely affect the evaluation.

The ENDO-LOK manufactured by the Olympic Medical Corporation comprises a rigid plastic tube into which an endotracheal tube may be placed. A longitudinal opening extends the length of the tube, permitting the device to be removed while the endotracheal tube is left in place. Extending vertically downward from the distal end of the tube is a rectangular plastic support arm that is attached to a flexible plastic bar. The endotracheal tube is held in place within the tubular bite block by a strap that is attached to a plastic flange extending perpendicularly from the support arm. The entire device is held in place by a strap adapted to encircle the patient's neck.

The BITE BLOCK AND DENTAL GUARD manufactured by the American Hospital Supply Corporation comprises a teeth-engaging urethane mouthpiece. A rectangular urethane element extends forwardly from a wedge provided at the back of the mouthpiece, to which an endotracheal tube may be taped. Guedel-type endotracheal tube devices consist of a plastic tube that is bent to the desired radius and is of sufficient length to allow insertion into the patient's throat. An oval flange extends perpendicularly from the distal end of the Guedel devices. Berman-type endotracheal tube devices consist of two parallel blades of plastic bent to the desired radius and connected longitudinally by a perpendicular wall between the two blades. A semi-circular flange extends perpendicularly from each blade to form an oval-shaped stop at the distal end of the device.

The ENDOTRACHEAL TUBE HOLDER manufactured by Portex, Incorporated comprises an endotracheal tube device consisting of a U-shaped channel which functions as a bite block and endotracheal tube holder. The device is held in place by cotton tape attached to a flexible frame at the distal end of the channel.

The AIRWAYS manufactured by Portex, Incorporated comprises airways of two designs. Guedel-type endotracheal tube devices consist of a plastic tube that is bent to the desired radius and is of sufficient length to allow insertion into the subject's throat. An oval flange extends perpendicularly from the distal end of the Guedel devices. Berman-type endotracheal tube devices consist of two parallel blades of plastic bent to the desired radius and connected longitudinally by a perpendicular wall between the two blades. A semi-circular flange extends perpendicularly from each blade to form an oval-shaped stop at the distal end of the device.

Such devices, however, have not satisfactorily provided a safe, effective, and inexpensive device capable of protecting an endotracheal tube from damage or occlusion.

SUMMARY OF THE INVENTION

The present invention provides a device for removably receiving an endotracheal tube or other medical apparatus including a substantially straight, cylindrical tube member having a proximal end and a distal end. The tube member has disposed therethrough a bore for removably receiving and passing an external medical apparatus. The tube member is adapted to be tightly received over the endotracheal tube after the endotracheal tube has been inserted. The proximal and distal ends of the tube member are rounded to prevent damage to the endotracheal tube. Means for securing the distal end of the tube member to an endotracheal tube or other medical apparatus consist of integrally formed substantially parallel ridges on the peripheral surface of the tube member. The ridges extend from the distal end of the tube member a sufficient distance to provide a surface to which adhesive or other suitable tape may be attached. A circumferential band of contrasting color extends around the tube member at a sufficient distance from the proximal end to indicate proper positioning of the device. The endotracheal tube protector is integrally formed from a high-strength plastic material such as polyurethane or other suitable surgical material to provide a durable tube that will not harm the teeth of the patient. Endotracheal tube protectors of the present invention may be made in various sizes to tightly receive and secure any size endotracheal tube.

One of the most serious disadvantages attendant known endotracheal tube protector devices is the fact that when a tube protector device is placed into the throat of the patient, a substantial gag reflex is elicited which is distressing for the patient and troublesome for the inserter of the device. Thus, such devices are not suitable for use with conscious subjects who are not anesthetized.

Further, endotracheal tube protectors which extend into the throat of the patient often cause trauma to the sensitive tissue of the mouth and throat.

In addition, endotracheal tube protector devices which are of complex construction are not only difficult to use, but are expensive to manufacture which militates against disposal of the device after use.

It is an object of the present invention to provide an endotracheal tube protector which may be manufactured in various sizes so as to tightly receive an endotracheal tube of any size.

Another object of the present invention is to provide an endotracheal tube protector which is easy to use and inexpensive to manufacture.

Further objects and details of the present invention will become apparent to those skilled in the art upon reading the following specification, appended claims, and the accompanying drawing.

DETAILED DESCRIPTION OF PREFERRED EMBODIMENTS

Figure 1:
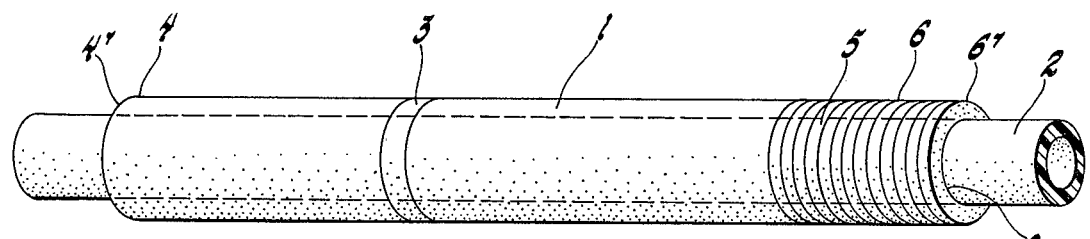
FIG. 1 illustrates a perspective view of the oral endotracheal tube protector in accordance with a preferred embodiment of the present invention with an external endotracheal tube passing therethrough.

With reference to FIG. 1, there is depicted the novel oral endotracheal tube protector device according to the present invention. The device includes a substantially straight tube member 1 having a bore 8 extending therethrough. An external endotracheal tube 2, which is well known in the art, is removably received in the bore 8 and passes through tube member 1 via the bore 8.

A circumferential band 3, which preferably is of a color contrasting with that of tube member 1, is provided a sufficient distance from the proximal end 4 of tube member 1 to indicate the point where the teeth of the patient 7 should rest, thereby consistently ensuring the proper positioning of tube member 1.

Substantially-parallel, circumferential ridges 5 are integrally formed on the peripheral surface of tube member 1 at the distal end 6 thereof. The ridges 5 are of substantially uniform height or diameter and extend from the distal end 6 of tube member 1 toward the proximal end 4 a sufficient distance to provide a corrugated surface thereon. The edge 6' of the distal end 6 and edge 4' of the proximal end 4 are rounded to prevent damage to the endotracheal tube and the patient 7.

Figure 2:
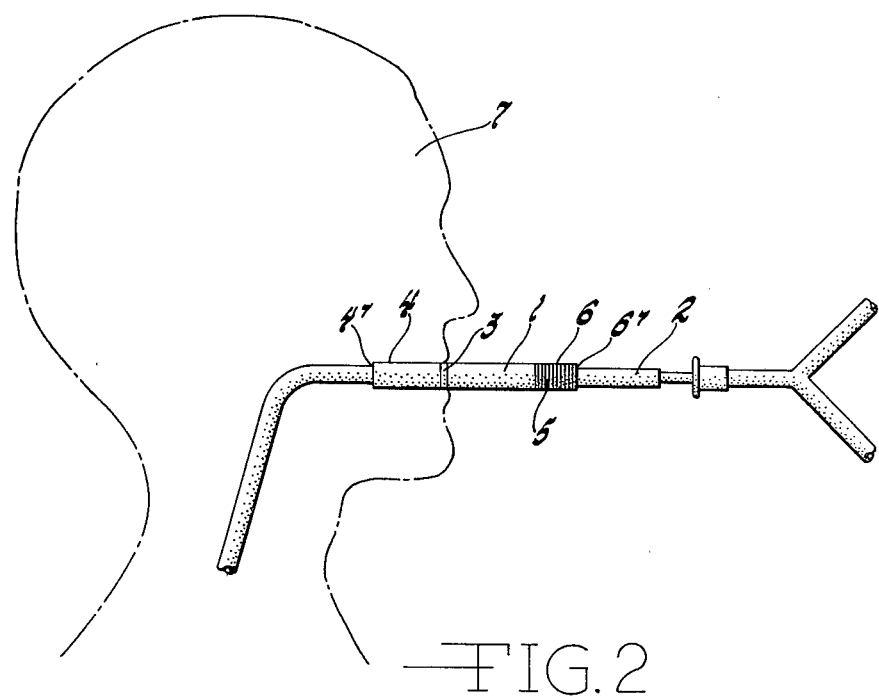
FIG. 2 depicts a side elevational view of the oral endotracheal tube protector in use.

Referring now to FIG. 2, the tube member 1 is illustrated in the operative position thereof, and the proper use of the device will now be described. The patient 7 is intubated through the oral route, and the cuff on the endotracheal tube 2 is inflated. An Ambu bag, which is well known in the art, is attached to the endotracheal tube 2 via an adapter, which is also well known in the art, and breathing is checked for symmetry. When the endotracheal tube 2 position appears to be proper and adequate, the Ambu bag and adapter are removed.

The bore 8 at the proximal end 4 of tube member 1 is brought into engagement with endotracheal tube 2, and tube member 1 is then slidably placed over endotracheal tube 2. Tube member 1 is advanced into the mouth of the patient until his teeth engage circumferential band 3 which indicates proper positioning of the tube member 1.

As tube member 1 does not extend into the patient's 7 throat, no significant gag reflex is elicited. After tube member 1 is advanced to the proper position, the adapter is replaced and the patient 7 is ventilated manually or by a mechanical ventilator. Distal end 6 of tube member 1 is then firmly taped to endotracheal tube 2, and the tube member 1 is taped to the face of the patient 7.

Tube member 1 is easily removed by the reversal of the abovementioned steps.

Although there have been described what are of present considered to be the preferred embodiments of the invention, it will be understood that various modifications may be made therein, and it is intended to cover in the appended claims all such modifications as fall within the true spirit and scope of the invention.

I claim:

1. A tube member for removably receiving an endotracheal tube having a proximal end portion adapted to be inserted into a trachea of a patient and a distal end portion adapted to extend exterior to the mouth of a patient, comprising:
cylinder means having a bore extending therethrough for removably receiving and passing an endotracheal tube therethrough;
said cylinder means having a proximal end portion, an intermediate portion and distal end portion;
said proximal end portion and intermediate portion having a continuous, uninterrupted constant diameter, cylindrical outer surface;
said distal end portion of said cylinder means having first means integral therewith for securing said distal end portion to the distal end portion of said endotracheal tube, said first means comprising said distal end portion of said cylinder means having an uneven outer surface to which tape may be attached; and said cylinder means having a length with respect to said endotracheal tube such that, when said endotracheal tube is inserted with the trachea and said cylinder means is in its operative position on said endotracheal tube with said distal end portion of said cylinder means secured to the distal end portion of said endotracheal tube, said proximal end portion of said cylinder means is disposed within the mouth and terminates substantially forwardly of the throat of a patient and said intermediate portion and distal end portion extend exterior to the mouth of the patient.

2. A tube member according to claim 1, wherein:

said first means for securing said distal end portion of said cylinder means to the distal end portion of said endotracheal tube comprises integrally-formed, substantially-parallel, circumferential ridges on the peripheral surface of said distal end portion of said cylinder means; and said circumferential ridges have a substantially uniform height or diameter.

3. A tube member according to claim 2, wherein:

said integrally-formed, substantially parallel, circumferential ridges extend over said distal end portion of said cylinder means a sufficient distance to provide a corrugated surface to which tape may be attached.

4. A tube member according to claim 1, wherein:

said cylinder means is integrally formed from a high-strength plastic material.

5. A tube member according to claim 1, wherein:

said cylinder means is substantially straight.

6. A tube member according to claim 1 or 3, wherein:

said proximal and distal end portions of said cylinder means have rounded edges.

7. A tube member according to claim 1, including:

second means for positioning the proximal end portion of said cylinder means in the mouth of a patient.

8. A tube member according to claim 7, wherein:

said second means for positioning the proximal end portion of said cylinder means in the mouth of a patient comprises a circumferential band extending around said cylinder means between said proximal end portion and intermediate portion to indicate proper positioning of said proximal end portion in the mouth of a patient.

9. A tube member according to claim 7, wherein:

said circumferential band is of a color contrasting with that of said cylinder means.

10. A tube member according to claim 1, wherein:

said bore extending through said tube member is cylindrical;

said cylinder means is dimensioned so as to be substantially tightly received and fitted over said endotracheal tube.

* * * * *